(12) United States Patent
Johnson, Jr. et al.

(10) Patent No.: US 7,691,838 B2
(45) Date of Patent: Apr. 6, 2010

(54) METHOD FOR TREATING DISEASES USING HSP90-INHIBITING AGENTS IN COMBINATION WITH ANTIMITOTICS

(75) Inventors: Robert Johnson, Jr., Lafayette, CA (US); Yiqing Zhou, Lafayette, CA (US); Thomas Müller, San Francisco, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 132 days.

(21) Appl. No.: 10/856,742

(22) Filed: May 27, 2004

(65) Prior Publication Data

US 2005/0020558 A1 Jan. 27, 2005

Related U.S. Application Data

(60) Provisional application No. 60/474,906, filed on May 30, 2003.

(51) Int. Cl.
*A01N 43/00* (2006.01)
*A61K 31/33* (2006.01)
*A01N 43/02* (2006.01)
*A61K 31/335* (2006.01)
*A01N 43/42* (2006.01)
*A61K 31/44* (2006.01)
*A01N 43/78* (2006.01)
*A61K 31/425* (2006.01)

(52) U.S. Cl. .................. 514/183; 514/449; 514/283; 514/365

(58) Field of Classification Search ............ None
See application file for complete search history.

(56) References Cited

U.S. PATENT DOCUMENTS

| | | | |
|---|---|---|---|
| 4,261,989 A | 4/1981 | Sasaki et al. | |
| 5,387,584 A | 2/1995 | Schnur | |
| 5,415,869 A | 5/1995 | Straubinger et al. | |
| 5,424,073 A | 6/1995 | Rahman et al. | |
| 5,510,118 A | 4/1996 | Bosch et al. | |
| 5,534,270 A | 7/1996 | De Castro | |
| 5,662,883 A | 9/1997 | Bagchi et al. | |
| 5,683,715 A | 11/1997 | Boni et al. | |
| 5,932,566 A | 8/1999 | Schnur et al. | |
| 5,977,163 A | 11/1999 | Li et al. | |
| 6,174,875 B1 | 1/2001 | DeFranco et al. | |
| 6,245,759 B1 | 6/2001 | Bilodeau et al. | |
| 6,306,874 B1 | 10/2001 | Fraley et al. | |
| 6,313,138 B1 | 11/2001 | Fraley et al. | |
| 6,682,758 B1 | 1/2004 | Tabibi et al. | |
| 6,872,715 B2 * | 3/2005 | Santi et al. | 514/183 |
| 6,946,456 B2 * | 9/2005 | Rosen et al. | 514/183 |
| 2004/0053909 A1 | 3/2004 | Snader et al. | |

FOREIGN PATENT DOCUMENTS

| | | |
|---|---|---|
| EP | 0 919 244 A2 | 6/1999 |
| WO | WO 98/30205 | 7/1998 |
| WO | WO 00/71163 | 11/2000 |
| WO | WO 01/10412 A1 | 2/2001 |
| WO | WO 02/09696 A1 | 2/2002 |
| WO | WO 02/15925 A1 | 2/2002 |
| WO | WO 02/28387 A1 * | 4/2002 |
| WO | WO 02/36171 A1 | 5/2002 |
| WO | WO 03/037860 A2 | 5/2003 |
| WO | WO 03/041643 A2 * | 5/2003 |
| WO | WO 03/050295 A2 | 6/2003 |
| WO | WO 03/082266 A1 | 10/2003 |
| WO | WO 03/086381 A1 | 10/2003 |
| WO | WO 2004/054624 A1 | 7/2004 |
| WO | WO 2004/087075 A2 | 10/2004 |
| WO | WO 2004/096224 A2 | 11/2004 |

OTHER PUBLICATIONS

Chou et al. "Desoxyepothilone B is Curative Against Human Tumor Xenografts That are Refractory to Paclitaxel". Proceedings of the National Academy of Sciences of the United States of America. 1998, 95(26), 15798-15802, abstract only.*

(Continued)

*Primary Examiner*—Ardin Marschel
*Assistant Examiner*—Leslie A Royds
(74) *Attorney, Agent, or Firm*—Elliott Korsen; Fox Rothschild LLP

(57) ABSTRACT

The present invention provides a method for treating cancer. The method involves the administration of an HSP90 inhibitor and an antimitotic, where the combined administration provides a synergistic effect. In one aspect of the invention, a method of treating cancer is provided where a subject is treated with a dose of an HSP90 inhibitor in one step and a dose of an antimitotic in another step. In another aspect of the invention, a method of treating cancer is provided where a subject is first treated with a dose of an HSP90 inhibitor and subsequently treated with a dose of an antimitotic. In another aspect of the invention, a method of treating cancer is provided where a subject is first treated with a dose of an antimitotic and subsequently treated with a dose of an HSP90 inhibitor.

2 Claims, No Drawings

OTHER PUBLICATIONS

STN Registry File No. 189453-10-9. "Epothilone D". Retrieved from STN Jan. 19, 2007. One page.*

U.S. Appl. No. 10/825,788, Tian et al.

L.Zhi-Yong et al., "Synergistic Effects of Geldanamycin and Antitumor Drugs," *Acta Pharmaceutica Sinica*, 2001, vol. 36(8), pp. 569-575.

D.M. Nguyen et al., "Enhancement of Paclitaxel-mediated Cytotoxicity in Lung Cancer Cells by . . . ," *Ann. Thorac Surg.*, 2001, vol. 72, pp. 371-379.

W. Jia et al., "Synergistic antileukemic interactions between 17-AAG and UCN-01 involve interruption of . . . ," *Blood*, 2003, vol. 102, No. 5, pp. 1824-1832.

Chemical Abstracts 130:291581 (Abstract of EP 0919244).

D.R. Ciocca, et al. "Response of human breast cancer cells to heat shock and chemotherapeutic drugs," *Cancer Res.*, 1992, vol. 52(13), pp. 3648-3654 (Abstract only).

D.S. Solit et al., "Inhibition of Heat Shock Protein 90 Function Down-Regulates Akt Kinase and . . . ," *Cancer Res.*, 2003, vol. 63, pp. 2139-2144.

I.A. Vasilevskaya et al., "Geldanamycin and its 17-Allylamino-17-Demethoxy Analogue Antagonize the . . . ," *Cancer Res.*, 2003, vol. 63, pp. 3241-3246.

M. Rahmani et al., "Coadministration of the Heat Shock Protein 90 Antagonist 17-Allylamino-17-demethoxygeldanamycin . . . ," *Cancer Res.*, 2003, vol. 63, pp. 8420-8427.

*Clinical Cancer Research*, vol. 5, Nov. 1999 (Supplement): Abstracts: Poster Session 3 (3788s).

E.A. Sausville, "Combining Cytotoxics and 17-Allylamino, 17-Demethoxygeldanamycin . . . ," *Clin. Can. Res.*, 2001, vol. 7, pp. 2155-2158.

P.M. Muenster,et al., "Modulation of Hsp90 Function by Ansamycins Sensitizes Breast Cancer Cells . . . ," *Clin. Can. Res.*, 2001, vol. 7, pp. 2228-2236.

S. Grant et al., "The use of cyclin-dependent kinase inhibitors alone or in combination with established . . . ," *Drug Resistance Updates*, 2003, vol. 6, pp. 15-26.

*European Journal of Cancer Supplements*, vol. 1(5), S6 (2003), p. S6.

D.C. Anderson, "The clinical potential of proteasome inhibition," *EJC Supplements*, vol. 2, No. 6 (2004), pp. 3-6.

L. Neckers et al, "Heat-shock protein 90 inhibitors as novel cancer chemotherapeutic agents," *Expert Opin. Emerging Drugs*, (2002), vol. 7(2), pp. 277-288.

C. Erlichman et al., "A phase I trial of 17-allylamino-geldanamycin (17AAG) in patients with advanced cancer," *J. of Clinical Oncology*, 2004, vol. 22, No. 14S, p. 3030.

D.M. Nguyen et al., "Sequence-dependent enhancement of paclitaxel toxicity in non-small cell lung cancer . . . ," *J. Thorac Cardiovasc. Surg.*, 1999, vol. 118, pp. 908-915.

M.V. Blagosklonny et al., "The Hsp90 inhibitor geldanamycin selectively sensitizes Bcr-Abl-expressing leukemia cells to cytotoxic chemotherapy," *Leukemia*, 2001, vol. 15, pp. 1537-1543.

R. Kroning et al., "Taxol can induce phosphorylation of BCL-2 in multiple myeloma cells and . . . ," *Leukemia Research*, 1998, vol. 22, No. 3, pp. 275-286.

I. Semenov et al., "Growth inhibition and apoptosis of myeloma cells by the CDK inhibitor flavopiridol," *Leukemia Research*, 2002, vol. 26, pp. 271-280.

E.G. Mimnaugh et al., "Simultaneous inhibition of hsp 90 and the proteasome promotes protein ubiquitination, causes endoplasmic reticulum-derived cytosolic . . . ," *Mol. Can. Ther.*, 2004, vol. 3(5), pp. 551-566.

A. Subbarao Sredhar et al., "Heat shock proteins in the regulation of apoptosis: new strategies in tumor therapy; A comprehensive review," *Pharmacology & Therapeutics*, 2004, vol. 10, pp. 227-257.

C.A. Byrd et al., "Heat shock protein 90 mediates macrophage activation by Taxol and bacterial lipopolysaccharide," *Proc. Natl. Acad. Sci.*, 1999, vol. 96, pp. 5645-5650.

M.P. Goetz et al., "The Hsp90 chaperone complex as a novel target for cancer therapy," *Annals of Oncology*, 2003, vol. 14, pp. 1169-1176.

P.N. Munster et al., "Phase I Trial of 17-(allylamino)-17-Demethoxygeldanamycin (17-AAG) in Patients (Pts) with Advanced Solid Malignancies," *Proceedings of ASCO*, vol. 20, 2001, General Poster, p. 327.

W.G. An, et al., "Depletion of p. 185$^{erbB2}$, Raf-1 and mutant p53 proteins by geldanamycin derivatives correlates with antiproliferative activity," *Cancer Chemother. Pharmacol.*, 1997, vol. 40, pp. 60-64.

R.D. Traver et al., "NAD(P)H:quinine oxidoreductase gene expression in human colon carcinoma cells: characterization of a mutation which . . . ," *Cancer Research*, 1992, vol. 52, Issue 4, pp. 797-802.

M.J. Egorin et al., "Metabolism of 17-(Allylamino)-17-demethoxygeldanamycin (NSC 330507) by . . . ," *Cancer Research*, 1998, vol. 58, pp. 2385-2396.

C.E. Stebbins et al., "Crystal Structure of an Hsp90-Geldanamycin Complex: Targeting of a Protein Chaperone by an Antitumor Agent," *Cell*, 1997, vol. 89, pp. 239-250.

C. Prodromou et al., "Identification and structural characterization of the ATP/ADP-Binding site in the Hsp90 Molecular Chaperone," *Cell*, 1997, vol. 90, pp. 65-75.

J. Zou et al., "Repression of heat stock transcription factor HSF1 activation by HSP90 (HSP90 Complex) that forms a stress-sensitive compled with HSF1," *Cell*, 1998, vol. 94, pp. 471-480.

R. Bagatell et al., "Induction of a heat shock factor 1-dependent stress response alters the cytotoxic activity of Hsp90-binding agents," *Clin. Can. Research*, 2000, vol. 6, pp. 3312-3318.

R. Bagatell et al., "Destabilization of steroid receptors by heat shock protein 90-binding drugs: A ligand-independent approach to hormonal therapy of breast cancer," *Clin. Can. Research*, 2001, vol. 7, pp. 2076-2084.

P.N. Muenster et al., "Modulation of Hsp90 function by ansamycins sensitizes breast cancer cells to chemotherapy-induced apoptosis in an Rb- and Schedule-dependent Manner," *Clin. Can. Research*, 2001, vol. 7, pp. 2228-2236.

A. Citri et al., "Drug-induced ubiquitylation and degradation of ErbB receptor tyrosine kinases: implications for cancer therapy," *The EMBO Journal*, 2002, vol. 21, No. 10, pp. 2407-2417.

W.B. Pratt et al., "Steroid receptor interactions with heat shock protein and immunophilin chaperones," (*download from* edrv.endojournals.org), 2005, vol. 18, No. 3, pp. 306-360.

R.I. Morimoto et al., "The heat-shock response: regulation and function of heat-shock proteins and molecular chaperones," *Essays Biochem.*, 1997, vol. 32, pp. 17-29 (abstract only).

Y. Murakami et al., "Induction of hsp 72/73 by herbimycin A, an inhibitor of transformation by tyrosine kinase oncogenes," *Exp. Cell Research*, 1991, vol. 195, Issue 2, pp. 338-344 (abstract only).

J.P. Grenert et al., "The amino-terminal domain of heat shock protein 90 (hsp90) that binds geldanamycin is an ATP/ADP switch domain that regulates . . . ," *J. of Biological Chemistry*, 1997, vol. 272, No. 38, pp. 23843-23850.

J.C. Young et al., "Hsp90: a specialized but essential protein-folding tool," *The Journal of Cell Biology*, 2001, vol. 154, pp. 267-273.

R.S. Hedge et al., "Short circuiting stress protein expression via a tyrosine kinase inhibitor, herbimycin A.," *J. Cell Physiol.*, 1995, vol. 165(1), pp. 186-200 (abstract only).

K. Richter et al., "Hsp90: Chaperoning Signal Transduction," *J. of Cell. Physiology*, 2001, vol. 188, pp. 281-290.

B. Lawson et al., "Geldanamycin, an hsp90/GRP94-binding drug, induces increased transcription of endoplasmic reticulum (ER) chaperones via the ER stress pathway," *J. of Cell. Physiology*, 1998, vol. 174, Issue 2, pp. 170-179.

B. Coh et al., "Explaining interindividual variability of docetaxel pharmacokinetics and pharmacodynamics in Asians through phenotyping and genotyping strategies," *J. of Clin. Oncology*, 2002, vol. 20, No. 17, pp. 3683-3690.

R.C. Schnur et al., "Inhibition of the oncogene product p185$^{erbB-2}$ in Vitro and in Vivo by geldanamycin and dihydrogeldanamycin derivatives," *J. Med. Chem.*, 1995, vol. 38, pp. 3806-3812.

R.C. Schnur et al., "*erbB*-2 Oncogene Inhibition by Geldanamycin Derivatives: Synthesis, Mechanism of Action, and Structure-Activity Relationships," *J. Med. Chem.*, 1995, vol. 38, pp. 3813-3820.

K.A. Gelmon et al., "Anticancer agents targeting signaling molecules and cancer cell environment: challenges for drug development?," *J. of the Nat'l. Cancer Institute*, 1999, vol. 91, No. 15, pp. 1281-1287.

L.R. Kelland et al., "DT-diaphorase expression and tumor cell sensitivity to 17-allylamino, 17-demethoxygeldanamycin, an inhibitor of heat stock . . . ," *J. of Nat'l. Cancer Institute*, 1999, vol. 91, No. 22, pp. 1940-1949.

D.F. Smith et al., "Identification of a 60-kilodalton stress-related protein, p60, which interacts with hsp90 and hsp70," *Mol. Cell. Biol.*, 1993, vol. 13, No. 2, pp. 869-876 (abstract only).

D.F. Smith et al., "Progesterone Receptor Structure and Function Altered by Geldanamycin, an hsp90-Binding Agent," *Mol. And Cell. Biol.*, 1995, vol. 15, No. 12, pp. 6804-6812.

R.L. Barent et al., "Analysis of FKBP51/FKBP52 Chimeras and Mutants for Hsp90 Binding and Association with Progesterone Receptor Complexes," *Mol. Endocrinology*, 1998, vol. 12, pp. 342-354.

J.L. Johnson et al., "Binding of p23 and hsp90 during assembly with the progesterone receptor," *Mol. Endocrinology*, 1995, vol. 9, pp. 670-678.

Y.S. Lin et al., "Co-regulation of *CYP3A4* and *CYP3A5* and Contribution to Hepatic and Intestinal Midazolam Metabolism," *Mol. Pharmacology*, 2002, vol. 62, No. 1, pp. 162-172.

P. Kuehl et al., "Sequence diversity in *CYP3A* promoters and characterization of the genetic basis of polymorphic *CYP3A5* expression," *Nature Genetics*, 2001, vol. 27, pp. 383-391.

E. Hustert et al., "The genetic determinants of the *CYP3A5* polymorphism," *Pharmacogenetics*, 2001, vol. 11(2), pp. 773-779 (abstract only).

L. Whitesell et al., "Inhibition of heat shock protein HSP90-pp60$^{v-src}$ heteroprotein complex formation by benzoquinone ansamycins: Essential role for stress . . . ," *Proc. Natl. Acad. Sci. USA*, 1994, vol. 91, pp. 8324-8328.

C. Schneider et al., "Pharmacologic shifting of a balance between protein refolding and degradation mediated by Hsp90," *Proc. Natl. Acad. Sci. USA*, 1996, vol. 93, pp. 14536-14541.

Agnew et al., "Clinical pharmacokinetics of 17-(allylamino)-17-demethoxy-geldanamycin and the active metabolite 17-(amino)-17-demethoxygeldanamycin . . . ," *Proc. Am. Assoc. Cancer Res.*, 2002, vol. 43, Abstract No. 1349.

A. Gaedigk et al., "NAD(P)H:quinine oxidoreductase: polymorphisms and allele frequencies in Caucasian, Chinese and Canadian Native Indian and Inuit populations," *Pharmacogenetics*, 1998, vol. 8, pp. 305-313.

F.U. Hartl et al., "Molecular Chaperones in the Cytosol: from Nascent Chain to Folded Protein," *Sciene*, 2002, vol. 295, pp. 1852-1858.

B. Lawson, "Geldanamycin, an hsp90/GRP94-binding drug, induces increased transcription of endoplasmic reticulum (ER) chaperones via the ER stress pathway," *J. of Cell. Physiology*, 1998, vol. 174, pp. 170-178.

P.N. Munster et al., "Phase I Trial of 17-(allylamino)-17-demethoxygeldanamycin (17-AAG) in patients (Pts) with advanced solid malignancies," *Proc. Am. Soc. Clin. Oncol.*, 2001, vol. 20, Abstract No. 327.

Munster et al., *Proc. Am. Assoc. Cancer Res.* 2001, 42, 68, abstract 364, "Modulation of HSP90 Function by Ansamycins Enhances Chemotherapy Induced Apoptosis in Breast Cancer Cell Lines in an RB and Schedule Dependent Manner."

Rani et al., *Eur. J. Cancer* 2002, 38, S58, abstract 184, "Biomarkers of anticancer activity of R115777 in combination with paclitaxel in a human breast cancer model in vitro".

Sauer et al., *Strahlenther Onkol.*, 2002, 178(3), 123-133, "New Molecular Targets of Breast Cancer Therapy".

* cited by examiner

METHOD FOR TREATING DISEASES USING HSP90-INHIBITING AGENTS IN COMBINATION WITH ANTIMITOTICS

CROSS REFERENCE TO RELATED U.S. PATENT APPLICATIONS

The present application claims the benefit of Provisional Patent Application No. 60/474,906, which was filed May 30, 2003, under 35 U.S.C. § 119(e). The provisional application is hereby incorporated-by-reference into this application for all purposes.

BACKGROUND OF THE INVENTION

Field of the Invention

This invention relates to methods for treating cancer in which an inhibitor of Heat Shock Protein 90 ("HSP90") is combined with an antimitotic. More particularly, this invention relates to combinations of the HSP90 inhibitor geldanamycin and its derivatives, especially 17-allylamino-17-desmethoxygeldanamycin ("17-AAG") and 17-(2-dimethylaminoethyl)amino-17-desmethoxygeldanamycin ("17-DMAG"), with an antimitotic (e.g., docetaxel, discodermolide, vinblastine, vincristine, vindesine, and epothilone D).

REFERENCES

Agnew et al., "Clinical pharmacokinetics of 17-(allylamino)-17-demethoxygeldanamycin and the active metabolite 17-(amino)-17-demethoxygeldanamycin given as a one-hour infusion daily for 5 days." AACR, 2002.

An et al., "Depletion of p185erbB2, Raf-1 and mutant p53 proteins by geldanamycin derivatives correlates with antiproliferative activity." *Cancer Chemother. Pharmacol.* 40:60-64, 1997.

Bagatell et al., "Induction of a heat shock factor 1-dependent stress response alters the cytotoxic activity of hsp90-binding agents." *Clin. Cancer Res.* 6:3312-3318, 2000.

Bagatell et al., "Destabilization of steroid receptors by heat shock protein 90-binding drugs: a ligand-independent approach to hormonal therapy of breast cancer." *Clin. Cancer Res.* 7:2076-2084, 2001.

Banerji et al., "A pharmacokinetically (PK)-pharmacodynamically (PD) driven Phase I trial of the HSP90 molecular chaperone inhibitor 17-allylamino-17-demethoxygeldanamycin (17-AAG)." AACR, 2002.

Barent et al., "Analysis of FKBP51/FKBP52 chimeras and mutants for Hsp90 binding and association with progesterone receptor complexes." *Mol. Endocrinol.* 12:342-354, 1998.

Bilodeau et al., "Tyrosine kinase inhibitors." U.S. Pat. No. 6,245,759 issued Jun. 12, 2001.

Citri et al., "Drug-induced ubiquitylation and degradation of ErbB receptor tyrosine dinases: implications for cancer chemotherapy." *EMBO Journal* 21:2407-2417, 2002.

Egorin et al., "Metabolism of 17-(allylamino)-17-demethoxygeldanamycin (NSC 330507) by murine and human hepatic preparations." *Cancer Res.* 58:2385-2396, 1998.

Fraley et al., "Tyrosine kinase inhibitors." U.S. Pat. No. 6,306,874 issued Oct. 23, 2001.

Fraley et al., "Tyrosine kinase inhibitors." U.S. Pat. No. 6,313,138 issued Nov. 6, 2001.

Gaidigk et al., "NAD (P)H:quinone oxidoreductase: polymorphisms and allele frequencies n Caucasian, Chinese and Canadian Native Indian and Inuit populations." *Pharmacogenetics* 8:305-313, 1998.

Gelmon et al., "Anticancer agents targeting signaling molecules and cancer cell environment: challenges for drug development?" *J. Natl. Cancer Inst.* 91:1281-1287, 1999.

Goetz et al., "The Hsp90 chaperone complex as a novel target for cancer therapy." *Ann. Oncol.* 14:1169-1176, 2003.

Goh et al., "Explaining interindividual variability of docetaxel pharmacokinetics and pharmacodynamics in Asians through phenotyping and genotyping strategies." *J. Clin. Oncol.* 20:3683-3690, 2002.

Grenert et al., "The amino-terminal domain of heat shock protein 90 (hsp90) that binds geldanamycin is an ATP/ADP switch domain that regulates hsp90 conformation." *J. Biol. Chem.* 272:23843-23850, 1997.

Johnson and Toft, "Binding of p23 and hsp90 during assembly with the progesterone receptor." *Mol. Endocrinol.* 9:670-678, 1995.

Hartl and Hayer-Hartl, "Molecular chaperones in the cytosol: from nascent chain to folded protein." *Science* 195:1852-1858, 2002.

Hegde et al., "Short circuiting stress protein expression via a tyrosine kinase inhibitor, herbimycin A." *J. Cell Physiol.* 165:186-200, 1995.

Hustert et al., "The genetic determinants of the CYP3A5 polymorphism." *Pharmacogenetics* 11:773-779, 2001.

Kelland et al., "DT-Diaphorase expression and tumor cell sensitivity to 17-allylamino, 17-demethoxygeldanamycin, an inhibitor of heat shock protein 90." *J. Natl. Cancer Inst.* 91:1940-1949, 1999.

Kuehl et al., "Sequence diversity in CYP3A promoters and characterization of the genetic basis of polymorphic CYP3A5 expression." *Nat. Genet.* 27:383-391, 2001.

Lawson et al., "Geldanamycin, an hsp90/GRP94-binding drug, induces increased transcription of endoplasmic reticulum (ER) chaperones via the ER stress pathway." *J. Cell Physiol.* 174:170-178, 1998.

Lin et al., "Co-regulation of CYP3A4 and CYP3A5 and contribution to hepatic and intestinal midazolam metabolism." *Mol. Pharmacol.* 62:162-172, 2002.

Morimoto et al., "The heat-shock response: regulation and function of heat-shock proteins and molecular chaperones." *Essays Biochem* 32:17-29, 1997.

Munster et al., "Phase I trial of 17-(allylamino)-17-demethoxygeldanamycin (17-AAG) in patients with advanced solid malignancies." *Proc. Am. Soc. Clin. Oncol,* 83a, 2001.

Munster et al., "Modulation of Hsp90 function by ansamycins sensitizes breast cancer cells to chemotherapy-induced apoptosis in an RB- and schedule-dependent manner." *Clin. Cancer Res.* 7:2228-2236, 2001.

Murakami et al., "Induction of hsp 72/73 by herbimycin A, an inhibitor of transformation by tyrosine kinase oncogenes." *Exp. Cell Res.* 195:338-344, 1991.

Pratt and Toft, "Steroid receptor interactions with heat shock protein and immunophilin chaperones." *Endocr. Rev.* 18:306-60, 1997.

Prodromou et al., "Identification and structural characterization of the ATP/ADP-binding site in the Hsp90 molecular chaperone." *Cell* 90:65-75, 1997.

Richter and Buchner, "Hsp90: chaperoning signal transduction." *J. Cell. Physiol.* 188:281-290, 2001.

Rosvold et al., "Identification of an NAD(P)H:quinone oxidoreductase polymorphism and its association with lung cancer and smoking." *Pharmacogenetics* 5:199-206, 1995.

Schneider et al., "Pharmacologic shifting of a balance between protein refolding and degradation mediated by Hsp90." *Proc. Natl. Acad. Sci. USA* 93:14536-14541, 1996.

Schnur et al., "erbB-2 oncogene inhibition by geldanamycin derivatives: synthesis, mechanism of action, and structure-activity relationships." *J. Med. Chem.* 38:3813-20, 1995.

Schnur et al., "Inhibition of the oncogene product p 185erbB-2 in vitro and in vivo by geldanamycin and dihydrogeldanamycin derivatives." *J. Med. Chem.* 38:3806-3812, 1995.

Smith et al., "Progesterone receptor structure and function altered by geldanamycin, an hsp90-binding agent." *Mol. Cell Biol.* 15:6804-6812, 1995.

Smith et al., "Identification of a 60-kilodalton stress-related protein, p60, which interacts with hsp90 and hsp70." *Mol. Cell Biol.* 13:869-876, 1993.

Stebbins et al., "Crystal structure of an Hsp90-geldanamycin complex: targeting of a protein chaperone by an antitumor agent." *Cell* 89:239-250, 1997.

Traver et al., "NAD(P)H:quinone oxidoreductase gene expression in human colon carcinoma cells: characterization of a mutation which modulates DT-diaphorase activity and mitomycin sensitivity." *Cancer Res.* 52:797-802, 1992.

Whitesell et al., "Inhibition of heat shock protein HSP90-pp60v-src heteroprotein complex formation by benzoquinone ansamycins: essential role for stress proteins in oncogenic transformation." *Proc. Natl. Acad. Sci. USA* 91:8324-8328, 1994.

Young et al., "Hsp90: a specialized but essential protein-folding tool." *J. Cell Biol.* 154:267-273, 2001.

Zou et al., "Repression of heat shock transcription factor HSF1 activation by HSP90 (HSP90 complex) that forms a stress-sensitive complex with HSF1." *Cell* 94:471-480, 1998.

Discussion

Geldanamycin (figure below, $R_{17}$=—$OCH_3$) is a benzoquinone ansamycin polyketide isolated from *Streptomyces geldanus*. Although originally discovered by screening microbial extracts for antibacterial and antiviral activity, geldanamycin was later found to be cytotoxic to certain tumor cells in vitro and to reverse the morphology of cells transformed by the Rous sarcoma virus to a normal state.

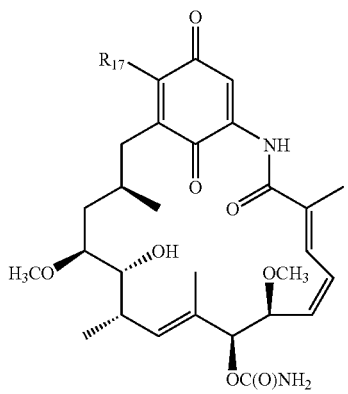

Geldanamycin's nanomolar potency and apparent specificity for aberrant protein kinase dependent tumor cells, as well as the discovery that its primary target in mammalian cells is the ubiquitous Hsp90 protein chaperone, has stimulated interest in the development of this compound as an anti-cancer drug. However, the association of unacceptable hepatotoxicity with the administration of geldanamycin led to its withdrawal from Phase I clinical trials.

More recently, attention has focused on 17-amino derivatives of geldanamycin, in particular 17-(allylamino)-17-desmethoxygeldanamycin ("17-AAG", $R_{17}$=NCH$_2$CH=CH$_2$). This compound has reduced hepatotoxicity while maintaining useful Hsp90 binding. Certain other 17-amino derivatives of geldanamycin, 11-oxogeldanamycin, and 5,6-dihydrogeldanamycin, are disclosed in U.S. Pat. Nos. 4,261,989, 5,387,584 and 5,932,566, each of which is incorporated herein by reference. Treatment of cancer cells with geldanamycin or 17-AAG causes a retinoblastoma protein-dependent G1 block, mediated by down-regulation of the induction pathways for cyclin D-cyclin dependent cdk4 and cdk6 protein kinase activity. Cell cycle arrest is followed by differentiation and apoptosis. G1 progression is unaffected by geldanamycin or 17-AAG in cells with mutated retinoblastoma protein; these cells undergo cell cycle arrest after mitosis, again followed by apoptosis.

The above-described mechanism of geldanamycin and 17-AAG appears to be a common mode of action among the benzoquinone ansamycins that further includes binding to Hsp90 and subsequent degradation of Hsp90-associated client proteins. Among the most sensitive client protein targets of the benzoquinone ansamycins are the Her kinases (also known as ErbB), Raf, Met tyrosine kinase, and the steroid receptors. Hsp90 is also involved in the cellular response to stress, including heat, radiation, and toxins. Certain benzoquinone ansamycins, such as 17-AAG, have thus been studied to determine their interaction with cytotoxins that do not target Hsp90 client proteins.

U.S. Pat. Nos. 6,245,759, 6,306,874 and 6,313,138, each of which is incorporated herein by reference, disclose compositions comprising certain tyrosine kinase inhibitors together with 17-AAG and methods for treating cancer with such compositions. Münster, et al., "Modulation of Hsp90 function by ansamycins sensitizes breast cancer cells to chemotherapy-induced apoptosis in an RB- and schedule-dependent manner," Clinical Cancer Research (2001) 7:2228-2236, discloses that 17-AAG sensitizes cells in culture to the cytotoxic effects of Paclitaxel and doxorubicin. The Münster reference further discloses that the sensitization towards paclitaxel by 17-AAG is schedule-dependent in retinoblastoma protein-producing cells due to the action of these two drugs at different stages of the cell cycle: treatment of cells with a combination of paclitaxel and 17-AAG is reported to give synergistic apoptosis, while pretreatment of cells with 17-AAG followed by treatment with paclitaxel is reported to result in abrogation of apoptosis. Treatment of cells with paclitaxel followed by treatment with 17-AAG 4 hours later is reported to show a synergistic effect similar to coincident treatment.

Citri, et al., "Drug-induced ubiquitylation and degradation of ErbB receptor tyrosine kinases: implications for cancer chemotherapy," EMBO Journal (2002) 21:2407-2417, discloses an additive effect upon co-administration of geldanamycin and an irreversible protein kinase inhibitor, CI-1033, on growth of ErbB2-expressing cancer cells in vitro. In contrast, an antagonistic effect of CI-1033 and anti-ErB2 antibody, Herceptin is disclosed.

Thus, while there has been a great deal of research interest in the benzoquinone ansamycins, particularly geldanamycin and 17-AAG, there remains a need for effective therapeutic regimens to treat cancer or other disease conditions characterized by undesired cellular hyperproliferation using such compounds, whether alone or in combination with other agents.

SUMMARY OF THE INVENTION

The present invention provides a method for treating cancer. The method involves the administration of an HSP90 inhibitor and an antimitotic, where the combined administration provides a synergistic effect.

In one aspect of the invention, a method of treating cancer is provided where a subject is treated with a dose of an HSP90 inhibitor in one step and a dose of an antimitotic in another step.

In another aspect of the invention, a method of treating cancer is provided where a subject is first treated with a dose of an HSP90 inhibitor and subsequently treated with a dose of an antimitotic.

In another aspect of the invention, a method of treating cancer is provided where a subject is first treated with a dose of an antimitotic and subsequently treated with a dose of an HSP90 inhibitor.

In another aspect of the invention, a method of treating cancer is provided where a subject is first treated with a dose of an antimitotic (e.g., docetaxel, vinblastine, vincristine, vindesine, and epothilone D). After waiting for a period of time sufficient to allow development of a substantially efficacious response of the antimitotic, a formulation comprising a synergistic dose of a benzoquinone ansamycin together with a second sub-toxic dose of the antimitotic is administered.

In another aspect of the invention, a method of treating cancer is provided where a subject is treated first with a dose of a benzoquinone ansamycin, and second, a dose of an antimitotic. After waiting for a period of time sufficient to allow development of a substantially efficacious response of the antimitotic, a formulation comprising a synergistic dose of a benzoquinone ansamycin together with a second sub-toxic dose of the antimitotic drug is administered.

In another aspect of the invention, a method for treating cancer is provided where a subject is treated with a dose of an HSP90 inhibitor in one step and a dose of an antimitotic in another step, and where a side effect profile for the combined, administered drugs is substantially better than for the antimitotic alone.

In another aspect of the invention, a method for treating breast or colorectal cancer is provided where a subject is treated with a dose of an HSP90 inhibitor in one step and a dose of an antimitotic in another step. The HSP90 inhibitor for this aspect is typically 17-AAG, while the antimitotic is usually docetaxel, vinblastine, vincristine, vindesine, or epothilone D. For the treatment of colorectal cancer, the antimitotic is typically administered before the 17-AAG; for the treatment of breast cancer, the antimitotic is typically administered after the 17-AAG. Where the antimitotic is epothilone D, it is oftentimes administered before the 17-AAG for the treatment of breast cancer.

Definitions

"Antimitotic" refers to a drug that inhibits or prevents mitosis or prodrugs thereof, excepting out antibiotics and enzyme inhibitors. Examples of antimitotics include, without limitation, vinblastine, vincristine, vindesine, vinorelbine, paclitaxel, docetaxel, discodermolide, epothilone D, etoposide, and teniposide.

"HSP90 inhibitor" refers to a compound that inhibits the activity of heat shock protein 90, which is a cellular protein responsible for chaperoning multiple client proteins necessary for cell signaling, proliferation and survival. One class of HSP90 inhibitors is the benzoquinone ansamycins. Examples of such compounds include, without limitation, geldanamycin and geldanamycin derivatives (e.g., 17-allylamino-17-desmethoxy-geldanamycin ("17-AAG") and 17-(2-dimethylaminoethyl)amino-17-desmethoxy-geldanamycin ("17-DMAG"). See Sasaki et al., U.S. Pat. No. 4,261,989 (1981) for synthesis of 17-AAG and Snader et al., US 2004/0053909 A1 (2004) for synthesis of 17-DMAG. In addition to 17-AAG and 17-DMAG, other preferred geldanamycin derivatives are 11-O-methyl-17-(2-(1-azetidinyl)ethyl)amino-17-demethoxygeldanamycin (A), 11-O-methyl-17-(2-dimethylaminoethyl)amino-17-demethoxygeldanamycin (B), and 11-O-methyl-17-(2-(1-pyrrolidinyl)ethyl)amino-17-demethoxygeldanamycin (C), whose synthesis is described in the co-pending commonly U.S. patent application of Tian et al., Ser. No. 10/825,788, filed Apr. 16, 2004, and in Tian et al., PCT application no. PCT/US04/11638, filed Apr. 16, 2004; the disclosures of which are incorporated herein by reference. Additional preferred geldanamycin derivatives are described in Santi et al., US 2003/0114450 A1 (2003), also incorporated by reference.

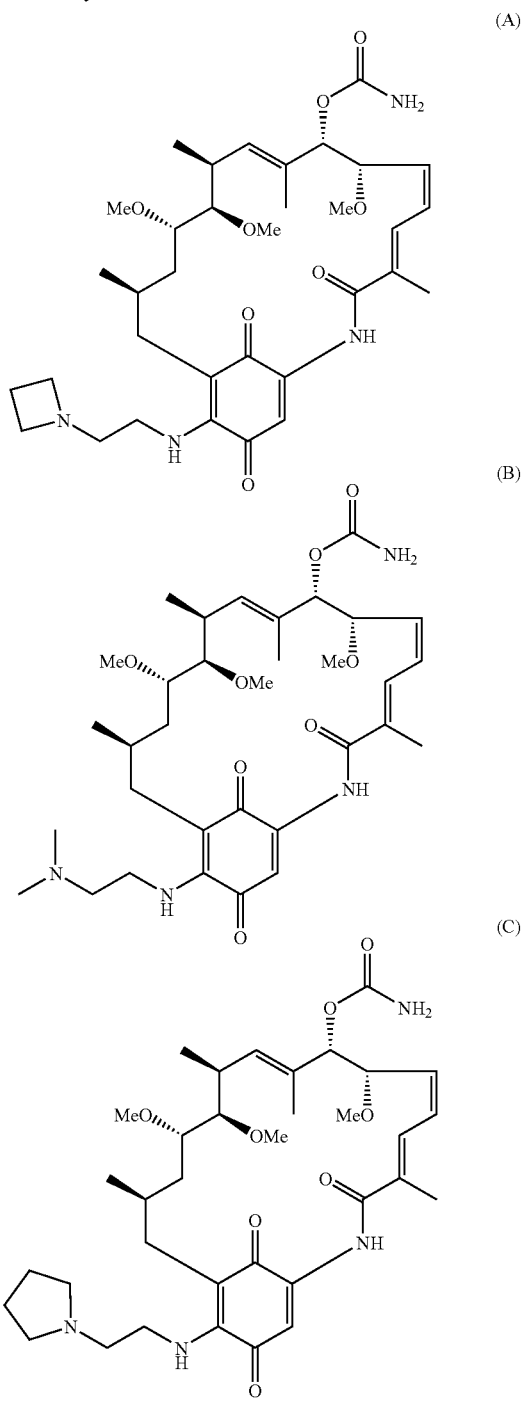

"MTD" refers to maximum tolerated dose. The MTD for a compound is determined using methods and materials known in the medical and pharmacological arts, for example through dose-escalation experiments. One or more patients is first treated with a low dose of the compound, typically about 10% of the dose anticipated to be therapeutic based on results of in vitro cell culture experiments. The patients are observed for a period of time to determine the occurrence of toxicity. Toxicity is typically evidenced as the observation of one or more of the following symptoms: vomiting, diarrhea, peripheral neuropathy, ataxia, neutropenia, or elevation of liver enzymes. If no toxicity is observed, the dose is increased about 2-fold, and the patients are again observed for evidence of toxicity. This cycle is repeated until a dose producing evidence of toxicity is eached. The dose immediately preceding the onset of unacceptable toxicity is taken as the MTD.

"Side effects" refer to a number of toxicities typically seen upon treatment of a subject with an antineoplastic drug. Such toxicities include, without limitation, anemia, anorexia, bilirubin effects, dehydration, dermatology effects, diarrhea, dizziness, dyspnea, edema, fatigue, headache, hematemesis, hypokalemia, hypoxia, musculoskeletal effects, myalgia, nausea, neuro-sensory effects, pain, rash, serum glutamic oxaloacetic transaminase effects, serum glutamic pyruvic transaminase effects, stomatitis, sweating, taste effects, thrombocytopenia, voice change, and vomiting.

"Side effect grading" refers to National Cancer Institute common toxicity criteria (NCI CTC, Version 2). Grading runs from 1 to 4, with a grade of 4 representing the most serious toxicities.

Combination Therapy

The present invention provides a method for treating cancer. The method involves the administration of an HSP90 inhibitor and an antimitotic, where the combined administration provides a synergistic effect.

Suitable HSP90 inhibitors used in the present invention include benzoquinone ansamycins. Typically, the benzoquinone ansamycin is geldanamycin or a geldanamycin derivative. Preferably, the benzoquinone ansamycin is a geldanamycin derivative selected from a group consisting of 17-allylamino-17-desmethoxy-geldanamycin ("17-AAG") and 17-(2-dimethylaminoethyl)amino-17-desmethoxy-geldanamycin ("17-DMAG").

Antimitotics employed in the present method include, without limitation, vinblastine, vincristine, vindesine, vinorelbine, paclitaxel, docetaxel, epothilone D, etoposide, and teniposide.

The dose of antimitotic used as a partner in combination therapy with an HSP90 inhibitor (e.g., benzoquinone ansamycin) is determined based on the maximum tolerated dose observed when the antimitotic is used as the sole therapeutic agent. In one embodiment of the invention, the dose of antimitotic when used in combination therapy with a benzoquinone ansamycin is the MTD. In other embodiments of the invention, the dose of antimitotic when used in combination therapy with a benzoquinone ansamycin is between about 1% of the MTD and the MTD, between about 5% of the MTD and the MTD, between about 5% of the MTD and 75% of the MTD, or between about 25% of the MTD and 75% of the MTD.

Use of the benzoquinone ansamycin allows for use of a lower therapeutic dose of an antimitotic, thus significantly widening the therapeutic window for treatment. In one embodiment, the therapeutic dose of antimitotic is lowered by at least about 10%. In other embodiments the therapeutic dose is lowered from about 10% to 20%, from about 20% to 50%, from about 50% to 200%, or from about 100% to 1,000%.

For the treatment of a variety of carcinomas, the recommended intravenous dose of various antimitotics is as follows: vinblastine (for adults)—administered once/week with an initial dose of 3.7 mg/m$^2$, with graded doses of 5.5, 7.4, 9.25 and 11.1 mg/m$^2$ at 7 day intervals; vincristine (for adults)—administered once/week with an initial dose of 0.4 to 1.4 mg/m$^2$; vindesine—administered at a dose of 3 mg/m$^2$; vinorelbine—30 mg/m$^2$/week; paclitaxel—135 mg/m$^2$ given IV over 3 hours once every 3 weeks (metastatic ovarian cancer, advanced ovarian cancer, and AIDS-related Kaposi's sarcoma) and 175 mg/m$^2$ given IV over 3 hours once every 3 weeks (metastatic breast cancer); docetaxel—60-100 mg/m$^2$ given over 1 hour once every 3 weeks; epothilone D—100 mg/m$^2$ once per week; etoposide—50 to 100 mg/m$^2$ for 5 days or 100 mg/m$^2$ on alternate days for three doses (testicular cancer) and 50 to 120 mg/m$^2$ per day intravenously for 3 days or 50 mg per day orally for 21 days (small cell lung carcinoma); and, teniposide—50 mg/m$^2$ per day for 5 days to 165 mg/m$^2$ per day twice weekly (lymphoblastic leukemia).

The synergistic dose of the benzoquinone ansamycin used in combination therapy is determined based on the maximum tolerated dose observed when the benzoquinone ansamycin is used as the sole therapeutic agent. Clinical trials have determined an MTD for 17-AAG of about 40 mg/m$^2$ utilizing a daily×5 schedule, an MTD of about 220 mg/m$^2$ utilizing a twice-weekly regimen, and an MTD of about 308 mg/m$^2$ utilizing a once-weekly regimen. In one embodiment of the invention, the dose of the benzoquinone ansamycin when used in combination therapy is the MTD. In other embodiments of the invention, the does of the benzoquinone ansamycin when used in combination therapy is between about 1% of the MTD and the MTD, between about 5% of the MTD and the MTD, between about 5% of the MTD and 75% of the MTD, or between about 25% of the MTD and 75% of the MTD.

Where the benzoquinone ansamycin is 17-AAG, and the administration of compound is weekly, its therapeutic dose is typically between 50 mg/m$^2$ and 450 mg/m$^2$. Preferably, the dose is between 150 mg/m$^2$ and 350 mg/m$^2$, and about 308 mg/m$^2$ is especially preferred. Where the administration of compound is biweekly (i.e., twice per week), the therapeutic dose of 17-AAG is typically between 50 mg/m$^2$ and 250 mg/m$^2$. Preferably, the dose is between 150 mg/m$^2$ and 250 mg/m$^2$, and about 220 mg/m$^2$ is especially preferred.

Where the present method involves the administration of 17-AAG and vinblastine, a dosage regimen involving one or two administrations of the combination per week is typical. Tables 1 and 2 below show a number of vinblastine/17-AAG dosage combinations (i.e., dosage combinations 0001 to 0096).

TABLE 1

| Vinblastine/17-AAG dosage combinations. | | | | |
| --- | --- | --- | --- | --- |
| | 30-100 mg/m$^2$ 17-AAG | 100-150 mg/m$^2$ 17-AAG | 150-200 mg/m$^2$ 17-AAG | 200-250 mg/m$^2$ 17-AAG |
| 0-1 mg/m$^2$ vinblastine | 0001 | 0002 | 0003 | 0004 |
| 1-2 mg/m$^2$ vinblastine | 0005 | 0006 | 0007 | 0008 |
| 2-3 mg/m$^2$ vinblastine | 0009 | 0010 | 0011 | 0012 |
| 3-4 mg/m$^2$ vinblastine | 0013 | 0014 | 0015 | 0016 |
| 4-5 mg/m$^2$ vinblastine | 0017 | 0018 | 0019 | 0020 |
| 5-6 mg/m$^2$ vinblastine | 0021 | 0022 | 0023 | 0024 |
| 6-7 mg/m$^2$ vinblastine | 0025 | 0026 | 0027 | 0028 |
| 7-8 mg/m$^2$ vinblastine | 0029 | 0030 | 0031 | 0032 |
| 8-9 mg/m$^2$ vinblastine | 0033 | 0034 | 0035 | 0036 |
| 9-10 mg/m$^2$ vinblastine | 0037 | 0038 | 0039 | 0040 |
| 10-11 mg/m$^2$ vinblastine | 0041 | 0042 | 0043 | 0044 |
| 11-12 mg/m$^2$ vinblastine | 0045 | 0046 | 0047 | 0048 |

TABLE 2

Vinblastine/17-AAG dosage combinations continued.

| | 250-300 mg/m² 17-AAG | 300-350 mg/m² 17-AAG | 350-400 mg/m² 17-AAG | 400-450 mg/m² 17-AAG |
|---|---|---|---|---|
| 0-1 mg/m² vinblastine | 0049 | 0050 | 0051 | 0052 |
| 1-2 mg/m² vinblastine | 0053 | 0054 | 0055 | 0056 |
| 2-3 mg/m² vinblastine | 0057 | 0058 | 0059 | 0060 |
| 3-4 mg/m² vinblastine | 0061 | 0062 | 0063 | 0064 |
| 4-5 mg/m² vinblastine | 0065 | 0066 | 0067 | 0068 |
| 5-6 mg/m² vinblastine | 0069 | 0070 | 0071 | 0072 |
| 6-7 mg/m² vinblastine | 0073 | 0074 | 0075 | 0076 |
| 7-8 mg/m² vinblastine | 0077 | 0078 | 0079 | 0080 |
| 8-9 mg/m² vinblastine | 0081 | 0082 | 0083 | 0084 |
| 9-10 mg/m² vinblastine | 0085 | 0086 | 0087 | 0088 |
| 10-11 mg/m² vinblastine | 0089 | 0090 | 0091 | 0092 |
| 11-12 mg/m² vinblastine | 0093 | 0094 | 0095 | 0096 |

Where the present method involves the administration of 17-AAG and vincristine, a dosage regimen involving one or two administrations of the combination per week is typical. Tables 3 and 4 below show a number of vincristine/17-AAG dosage combinations (i.e., dosage combinations 0097 to 0176).

TABLE 3

Vincristine/17-AAG dosage combinations.

| | 30-100 mg/m² 17-AAG | 100-150 mg/m² 17-AAG | 150-200 mg/m² 17-AAG | 200-250 mg/m² 17-AAG |
|---|---|---|---|---|
| 0-0.2 mg/m² vincristine | 0097 | 0098 | 0099 | 0100 |
| 0.2-0.4 mg/m² vincristine | 0101 | 0102 | 0103 | 0104 |
| 0.4-0.6 mg/m² vincristine | 0105 | 0106 | 0107 | 0108 |
| 0.6-0.8 mg/m² vincristine | 0109 | 0110 | 0111 | 0112 |
| 0.8-1.0 mg/m² vincristine | 0113 | 0114 | 0115 | 0116 |
| 1.0-1.2 mg/m² vincristine | 0117 | 0118 | 0119 | 0120 |
| 1.2-1.4 mg/m² vincristine | 0121 | 0122 | 0123 | 0124 |
| 1.4-1.6 mg/m² vincristine | 0125 | 0126 | 0127 | 0128 |
| 1.6-1.8 mg/m² vincristine | 0129 | 0130 | 0131 | 0132 |
| 1.8-2.0 mg/m² vincristine | 0133 | 0134 | 0135 | 0136 |

TABLE 4

Vincristine/17-AAG dosage combinations continued.

| | 250-300 mg/m² 17-AAG | 300-350 mg/m² 17-AAG | 350-400 mg/m² 17-AAG | 400-450 mg/m² 17-AAG |
|---|---|---|---|---|
| 0-0.2 mg/m² vincristine | 0137 | 0138 | 0139 | 0140 |
| 0.2-0.4 mg/m² vincristine | 0141 | 0142 | 0143 | 0144 |
| 0.4-0.6 mg/m² vincristine | 0145 | 0146 | 0147 | 0148 |
| 0.6-0.8 mg/m² vincristine | 0149 | 0150 | 0151 | 0152 |
| 0.8-1.0 mg/m² vincristine | 0153 | 0154 | 0155 | 0156 |
| 1.0-1.2 mg/m² vincristine | 0157 | 0158 | 0159 | 0160 |
| 1.2-1.4 mg/m² vincristine | 0161 | 0162 | 0163 | 0164 |
| 1.4-1.6 mg/m² vincristine | 0165 | 0166 | 0167 | 0168 |
| 1.6-1.8 mg/m² vincristine | 0169 | 0170 | 0171 | 0172 |
| 1.8-2.0 mg/m² vincristine | 0173 | 0174 | 0175 | 0176 |

Where the present method involves the administration of 17-AAG and vindesine, a dosage regimen involving one or two administrations of the combination per week is typical. Tables 5 and 6 below show a number of vindesine/17-AAG dosage combinations (i.e., dosage combinations 0177 to 0256).

TABLE 5

Vindesine/17-AAG dosage combinations.

| | 30-100 mg/m² 17-AAG | 100-150 mg/m² 17-AAG | 150-200 mg/m² 17-AAG | 200-250 mg/m² 17-AAG |
|---|---|---|---|---|
| 0-0.3 mg/m² vindesine | 0177 | 0178 | 0179 | 0180 |
| 0.3-0.6 mg/m² vindesine | 0181 | 0182 | 0183 | 0184 |
| 0.6-0.9 mg/m² vindesine | 0185 | 0186 | 0187 | 0188 |
| 0.9-1.2 mg/m² vindesine | 0189 | 0190 | 0191 | 0192 |
| 1.2-1.5 mg/m² vindesine | 0193 | 0194 | 0195 | 0196 |
| 1.5-1.8 mg/m² vindesine | 0197 | 0198 | 0199 | 0200 |
| 1.8-2.1 mg/m² vindesine | 0201 | 0202 | 0203 | 0204 |
| 2.1-2.4 mg/m² vindesine | 0205 | 0206 | 0207 | 0208 |
| 2.4-2.7 mg/m² vindesine | 0209 | 0210 | 0211 | 0212 |
| 2.7-3.0 mg/m² vindesine | 0213 | 0214 | 0215 | 0216 |

TABLE 6

Vindesine/17-AAG dosage combinations continued.

| | 250-300 mg/m² 17-AAG | 300-350 mg/m² 17-AAG | 350-400 mg/m² 17-AAG | 400-450 mg/m² 17-AAG |
|---|---|---|---|---|
| 0-0.3 mg/m² vindesine | 0217 | 0218 | 0219 | 0220 |
| 0.3-0.6 mg/m² vindesine | 0221 | 0222 | 0223 | 0224 |

TABLE 6-continued

Vindesine/17-AAG dosage combinations continued.

| | 250-300 mg/m² 17-AAG | 300-350 mg/m² 17-AAG | 350-400 mg/m² 17-AAG | 400-450 mg/m² 17-AAG |
|---|---|---|---|---|
| 0.6-0.9 mg/m² vindesine | 0225 | 0226 | 0227 | 0228 |
| 0.9-1.2 mg/m² vindesine | 0229 | 0230 | 0231 | 0232 |
| 1.2-1.5 mg/m² vindesine | 0233 | 0234 | 0235 | 0236 |
| 1.5-1.8 mg/m² vindesine | 0237 | 0238 | 0239 | 0240 |
| 1.8-2.1 mg/m² vindesine | 0241 | 0242 | 0243 | 0244 |
| 2.1-2.4 mg/m² vindesine | 0245 | 0246 | 0247 | 0248 |
| 2.4-2.7 mg/m² vindesine | 0249 | 0250 | 0251 | 0252 |
| 2.7-3.0 mg/m² vindesine | 0253 | 0254 | 0255 | 0256 |

Where the present method involves the administration of 17-AAG and vinorelbine, a dosage regimen involving one or two administrations of the combination per week is typical. Tables 7 and 8 below show a number of vinorelbine/17-AAG dosage combinations (i.e., dosage combinations 0257 to 0336).

TABLE 7

Vinorelbine/17-AAG dosage combinations.

| | 30-100 mg/m² 17-AAG | 100-150 mg/m² 17-AAG | 150-200 mg/m² 17-AAG | 200-250 mg/m² 17-AAG |
|---|---|---|---|---|
| 0-3 mg/m² vinorelbine | 0257 | 0258 | 0259 | 0260 |
| 3-6 mg/m² vinorelbine | 0261 | 0262 | 0263 | 0264 |
| 6-9 mg/m² vinorelbine | 0265 | 0266 | 0267 | 0268 |
| 9-12 mg/m² vinorelbine | 0269 | 0270 | 0271 | 0272 |
| 12-15 mg/m² vinorelbine | 0273 | 0274 | 0275 | 0276 |
| 15-18 mg/m² vinorelbine | 0277 | 0278 | 0279 | 0280 |
| 18-21 mg/m² vinorelbine | 0281 | 0282 | 0283 | 0284 |
| 21-24 mg/m² vinorelbine | 0285 | 0286 | 0287 | 0288 |
| 24-27 mg/m² vinorelbine | 0289 | 0290 | 0291 | 0292 |
| 27-30 mg/m² vinorelbine | 0293 | 0294 | 0295 | 0296 |

TABLE 8

Vinorelbine/17-AAG dosage combinations continued.

| | 250-300 mg/m² 17-AAG | 300-350 mg/m² 17-AAG | 350-400 mg/m² 17-AAG | 400-450 mg/m² 17-AAG |
|---|---|---|---|---|
| 0-3 mg/m² vinorelbine | 0297 | 0298 | 0299 | 0300 |
| 3-6 mg/m² vinorelbine | 0301 | 0302 | 0303 | 0304 |
| 6-9 mg/m² vinorelbine | 0305 | 0306 | 0307 | 0308 |
| 9-12 mg/m² vinorelbine | 0309 | 0310 | 0311 | 0312 |
| 12-15 mg/m² vinorelbine | 0313 | 0314 | 0315 | 0316 |
| 15-18 mg/m² vinorelbine | 0317 | 0318 | 0319 | 0320 |
| 18-21 mg/m² vinorelbine | 0321 | 0322 | 0323 | 0324 |
| 21-24 mg/m² vinorelbine | 0325 | 0326 | 0327 | 0328 |
| 24-27 mg/m² vinorelbine | 0329 | 0330 | 0331 | 0332 |
| 27-30 mg/m² vinorelbine | 0333 | 0334 | 0335 | 0336 |

Where the present method involves the administration of 17-AAG and paclitaxel, a dosage regimen involving one or two administrations of the combination per week or longer (e.g., every 3 weeks) is typical. Tables 9 and 10 below show a number of paclitaxel/17-AAG dosage combinations (i.e., dosage combinations 0337 to 0408).

TABLE 9

Paclitaxel/17-AAG dosage combinations.

| | 30-100 mg/m² 17-AAG | 100-150 mg/m² 17-AAG | 150-200 mg/m² 17-AAG | 200-250 mg/m² 17-AAG |
|---|---|---|---|---|
| 0-20 mg/m² paclitaxel | 0337 | 0338 | 0339 | 0340 |
| 20-40 mg/m² paclitaxel | 0341 | 0342 | 0343 | 0344 |
| 40-60 mg/m² paclitaxel | 0345 | 0346 | 0347 | 0348 |
| 60-80 mg/m² paclitaxel | 0349 | 0350 | 0351 | 0352 |
| 80-100 mg/m² paclitaxel | 0353 | 0354 | 0355 | 0356 |
| 100-120 mg/m² paclitaxel | 0357 | 0358 | 0359 | 0360 |
| 120-140 mg/m² paclitaxel | 0361 | 0362 | 0363 | 0364 |
| 140-160 mg/m² paclitaxel | 0365 | 0366 | 0367 | 0368 |
| 160-180 mg/m² paclitaxel | 0369 | 0370 | 0371 | 0372 |

TABLE 10

Paclitaxel/17-AAG dosage combinations continued.

| | 250-300 mg/m² 17-AAG | 300-350 mg/m² 17-AAG | 350-400 mg/m² 17-AAG | 400-450 mg/m² 17-AAG |
|---|---|---|---|---|
| 0-20 mg/m² paclitaxel | 0373 | 0374 | 0375 | 0376 |
| 20-40 mg/m² paclitaxel | 0377 | 0378 | 0379 | 0380 |
| 40-60 mg/m² paclitaxel | 0381 | 0382 | 0383 | 0384 |
| 60-80 mg/m² paclitaxel | 0385 | 0386 | 0387 | 0388 |
| 80-100 mg/m² paclitaxel | 0389 | 0390 | 0391 | 0392 |
| 100-120 mg/m² paclitaxel | 0393 | 0394 | 0395 | 0396 |
| 120-140 mg/m² paclitaxel | 0397 | 0398 | 0399 | 0400 |

TABLE 10-continued

Paclitaxel/17-AAG dosage combinations continued.

| | 250-300 mg/m² 17-AAG | 300-350 mg/m² 17-AAG | 350-400 mg/m² 17-AAG | 400-450 mg/m² 17-AAG |
|---|---|---|---|---|
| 140-160 mg/m² paclitaxel | 0401 | 0402 | 0403 | 0404 |
| 160-180 mg/m² paclitaxel | 0405 | 0406 | 0407 | 0408 |

Where the present method involves the administration of 17-AAG and docetaxel, a dosage regimen involving one or two administrations of the combination per week or longer (e.g., every 3 weeks) is typical. Tables 11 and 12 below show a number of docetaxel/17-AAG dosage combinations (i.e., dosage combinations 0409 to 0488).

TABLE 11

Docetaxel/17-AAG dosage combinations.

| | 30-100 mg/m² 17-AAG | 100-150 mg/m² 17-AAG | 150-200 mg/m² 17-AAG | 200-250 mg/m² 17-AAG |
|---|---|---|---|---|
| 0-10 mg/m² docetaxel | 0409 | 0410 | 0411 | 0412 |
| 10-20 mg/m² docetaxel | 0413 | 0414 | 0415 | 0416 |
| 20-30 mg/m² docetaxel | 0417 | 0418 | 0419 | 0420 |
| 30-40 mg/m² docetaxel | 0421 | 0422 | 0423 | 0424 |
| 40-50 mg/m² docetaxel | 0425 | 0426 | 0427 | 0428 |
| 50-60 mg/m² docetaxel | 0429 | 0430 | 0431 | 0432 |
| 60-70 mg/m² docetaxel | 0433 | 0434 | 0435 | 0436 |
| 70-80 mg/m² docetaxel | 0437 | 0438 | 0439 | 0440 |
| 80-90 mg/m² docetaxel | 0441 | 0442 | 0443 | 0444 |
| 90-100 mg/m² docetaxel | 0445 | 0446 | 0447 | 0448 |

TABLE 12

Docetaxel/17-AAG dosage combinations continued.

| | 250-300 mg/m² 17-AAG | 300-350 mg/m² 17-AAG | 350-400 mg/m² 17-AAG | 400-450 mg/m² 17-AAG |
|---|---|---|---|---|
| 0-10 mg/m² docetaxel | 0449 | 0450 | 0451 | 0452 |
| 10-20 mg/m² docetaxel | 0453 | 0454 | 0455 | 0456 |
| 20-30 mg/m² docetaxel | 0457 | 0458 | 0459 | 0460 |
| 30-40 mg/m² docetaxel | 0461 | 0462 | 0463 | 0464 |
| 40-50 mg/m² docetaxel | 0465 | 0466 | 0467 | 0468 |
| 50-60 mg/m² docetaxel | 0469 | 0470 | 0471 | 0472 |
| 60-70 mg/m² docetaxel | 0473 | 0474 | 0475 | 0476 |
| 70-80 mg/m² docetaxel | 0477 | 0478 | 0479 | 0480 |
| 80-90 mg/m² docetaxel | 0481 | 0482 | 0483 | 0484 |
| 90-100 mg/m² docetaxel | 0485 | 0486 | 0487 | 0488 |

Where the present method involves the administration of 17-AAG and epothilone D, a dosage regimen involving one or two administrations of the combination per week or longer (e.g., every 3 weeks) is typical. Tables 13 and 14 below show a number of epothilone D/17-AAG dosage combinations (i.e., dosage combinations 0489 to 0558).

TABLE 13

Epothilone D/17-AAG dosage combinations.

| | 30-100 mg/m² 17-AAG | 100-150 mg/m² 17-AAG | 150-200 mg/m² 17-AAG | 200-250 mg/m² 17-AAG |
|---|---|---|---|---|
| 0-10 mg/m² epothilone D | 0489 | 0490 | 0491 | 0492 |
| 10-20 mg/m² epothilone D | 0493 | 0494 | 0495 | 0496 |
| 20-30 mg/m² epothilone D | 0497 | 0498 | 0499 | 0500 |
| 30-40 mg/m² epothilone D | 0501 | 0502 | 0503 | 0504 |
| 40-50 mg/m² epothilone D | 0505 | 0506 | 0507 | 0508 |
| 50-60 mg/m² epothilone D | 0509 | 0500 | 0501 | 0502 |
| 60-70 mg/m² epothilone D | 0503 | 0504 | 0505 | 0506 |
| 70-80 mg/m² epothilone D | 0507 | 0508 | 0509 | 0510 |
| 80-90 mg/m² epothilone D | 0511 | 0512 | 0513 | 0514 |
| 90-100 mg/m² epothilone D | 0515 | 0516 | 0517 | 0518 |

TABLE 14

Epothilone D/17-AAG dosage combinations continued.

| | 250-300 mg/m² 17-AAG | 300-350 mg/m² 17-AAG | 350-400 mg/m² 17-AAG | 400-450 mg/m² 17-AAG |
|---|---|---|---|---|
| 0-10 mg/m² epothilone D | 0519 | 0520 | 0521 | 0522 |
| 10-20 mg/m² epothilone D | 0523 | 0524 | 0525 | 0526 |
| 20-30 mg/m² epothilone D | 0527 | 0528 | 0529 | 0530 |
| 30-40 mg/m² epothilone D | 0531 | 0532 | 0533 | 0534 |
| 40-50 mg/m² epothilone D | 0535 | 0536 | 0537 | 0538 |
| 50-60 mg/m² epothilone D | 0539 | 0540 | 0541 | 0542 |
| 60-70 mg/m² epothilone D | 0543 | 0544 | 0545 | 0546 |
| 70-80 mg/m² epothilone D | 0547 | 0548 | 0549 | 0550 |
| 80-90 mg/m² epothilone D | 0551 | 0552 | 0553 | 0554 |
| 90-100 mg/m² epothilone D | 0555 | 0556 | 0557 | 0558 |

Where the present method involves the administration of 17-AAG and etoposide, a dosage regimen involving more than one or two administrations of the combination per week or is typical. Oftentimes the combination is administered 3, 4 or 5 times per week. Tables 15 and 16 below show a number of etoposide/17-AAG dosage combinations (i.e., dosage combinations 0559 to 0654).

TABLE 15

Etoposide/17-AAG dosage combinations.

|  | 30-100 mg/m² 17-AAG | 100-150 mg/m² 17-AAG | 150-200 mg/m² 17-AAG | 200-250 mg/m² 17-AAG |
|---|---|---|---|---|
| 0-10 mg/m² etoposide | 0559 | 0560 | 0561 | 0562 |
| 10-20 mg/m² etoposide | 0563 | 0564 | 0565 | 0566 |
| 20-30 mg/m² etoposide | 0567 | 0568 | 0569 | 0570 |
| 30-40 mg/m² etoposide | 0571 | 0572 | 0573 | 0574 |
| 40-50 mg/m² etoposide | 0575 | 0576 | 0577 | 0578 |
| 50-60 mg/m² etoposide | 0579 | 0580 | 0581 | 0582 |
| 60-70 mg/m² etoposide | 0583 | 0584 | 0585 | 0586 |
| 70-80 mg/m² etoposide | 0587 | 0588 | 0589 | 0590 |
| 80-90 mg/m² etoposide | 0591 | 0592 | 0593 | 0594 |
| 90-100 mg/m² etoposide | 0595 | 0596 | 0597 | 0598 |
| 100-110 mg/m² etoposide | 0599 | 0600 | 0601 | 0602 |
| 110-120 mg/m² etoposide | 0603 | 0604 | 0605 | 0606 |

TABLE 16

Etoposide/17-AAG dosage combinations continued.

|  | 250-300 mg/m² 17-AAG | 300-350 mg/m² 17-AAG | 350-400 mg/m² 17-AAG | 400-450 mg/m² 17-AAG |
|---|---|---|---|---|
| 0-10 mg/m² etoposide | 0607 | 0608 | 0609 | 0610 |
| 10-20 mg/m² etoposide | 0611 | 0612 | 0613 | 0614 |
| 20-30 mg/m² etoposide | 0615 | 0616 | 0617 | 0618 |
| 30-40 mg/m² etoposide | 0619 | 0620 | 0621 | 0622 |
| 40-50 mg/m² etoposide | 0623 | 0624 | 0625 | 0626 |
| 50-60 mg/m² etoposide | 0627 | 0628 | 0629 | 0630 |
| 60-70 mg/m² etoposide | 0631 | 0632 | 0633 | 0634 |
| 70-80 mg/m² etoposide | 0635 | 0636 | 0637 | 0638 |
| 80-90 mg/m² etoposide | 0639 | 0640 | 0641 | 0642 |
| 90-100 mg/m² etoposide | 0643 | 0644 | 0645 | 0646 |
| 100-110 mg/m² etoposide | 0647 | 0648 | 0649 | 0650 |
| 110-120 mg/m² etoposide | 0651 | 0652 | 0653 | 0654 |

Where the present method involves the administration of 17-AAG and teniposide, a dosage regimen involving more than one or two administrations of the combination per week or is typical. Oftentimes the combination is administered 3, 4 or 5 times per week. Tables 17 and 18 below show a number of teniposide/17-AAG dosage combinations (i.e., dosage combinations 0655 to 0742).

TABLE 17

Teniposide/17-AAG dosage combinations.

|  | 30-100 mg/m² 17-AAG | 100-150 mg/m² 17-AAG | 150-200 mg/m² 17-AAG | 200-250 mg/m² 17-AAG |
|---|---|---|---|---|
| 0-15 mg/m² teniposide | 0655 | 0656 | 0657 | 0658 |
| 15-30 mg/m² teniposide | 0659 | 0660 | 0661 | 0662 |
| 30-45 mg/m² teniposide | 0663 | 0664 | 0665 | 0666 |
| 45-60 mg/m² teniposide | 0667 | 0668 | 0669 | 0670 |
| 60-75 mg/m² teniposide | 0671 | 0672 | 0673 | 0674 |
| 75-90 mg/m² teniposide | 0675 | 0676 | 0677 | 0678 |
| 90-105 mg/m² teniposide | 0679 | 0680 | 0681 | 0682 |
| 105-120 mg/m² teniposide | 0683 | 0684 | 0685 | 0686 |
| 120-135 mg/m² teniposide | 0687 | 0688 | 0689 | 0690 |
| 135-150 mg/m² teniposide | 0691 | 0692 | 0693 | 0694 |
| 150-165 mg/m² teniposide | 0695 | 0696 | 0697 | 0698 |

TABLE 18

Teniposide/17-AAG dosage combinations continued.

|  | 250-300 mg/m² 17-AAG | 300-350 mg/m² 17-AAG | 350-400 mg/m² 17-AAG | 400-450 mg/m² 17-AAG |
|---|---|---|---|---|
| 0-15 mg/m² teniposide | 0699 | 0700 | 0701 | 0702 |
| 15-30 mg/m² teniposide | 0703 | 0704 | 0705 | 0706 |
| 30-45 mg/m² teniposide | 0707 | 0708 | 0709 | 0710 |
| 45-60 mg/m² teniposide | 0711 | 0712 | 0713 | 0714 |
| 60-75 mg/m² teniposide | 0715 | 0716 | 0717 | 0718 |
| 75-90 mg/m² teniposide | 0719 | 0720 | 0721 | 0722 |
| 90-105 mg/m² teniposide | 0723 | 0724 | 0725 | 0726 |
| 105-120 mg/m² teniposide | 0727 | 0728 | 0729 | 0730 |
| 120-135 mg/m² teniposide | 0731 | 0732 | 0733 | 0734 |
| 135-150 mg/m² teniposide | 0735 | 0736 | 0737 | 0738 |
| 150-165 mg/m² teniposide | 0739 | 0740 | 0741 | 0742 |

The method of the present invention may be carried out in at least two basic ways. A subject may first be treated with a dose on an HSP90 inhibitor and subsequently be treated with a dose of an antimitotic. Alternatively, the subject may first be treated with a dose of an antimitotic and subsequently be treated with a dose of an HSP90 inhibitor. The appropriate dosing regimen depends on the particular antimitotic employed.

In another aspect of the invention, a subject is first treated with a dose of a an antimitotic (e.g., docetaxel, viblastine, vincristine, vindesine, or epothilone D). After waiting for a period of time sufficient to allow development of a substantially efficacious response of the antimitotic, a formulation comprising a synergistic dose of a benzoquinone ansamycin together with a second sub-toxic dose of the antimitotic is administered. In general, the appropriate period of time sufficient to allow development of a substantially efficacious response to the antimitotic will depend upon the pharmacokinetics of the antimitotic, and will have been determined during clinical trials of therapy using the antimitotic alone. In one embodiment of the invention, the period of time sufficient to allow development of a substantially efficacious response to the antimitotic is between about 1 hour and 96 hours. In another aspect of the invention, the period of time sufficient to allow development of a substantially efficacious response to the antimitotic is between about 2 hours and 48 hours. In another embodiment of the invention, the period of time sufficient to allow development of a substantially efficacious response to the antimitotic is between about 4 hours and 24 hours.

In another aspect of the invention, a subject is treated first with one of the above-described benzoquinone ansamycins, and second, a dose of an antimitotic, such as, but not limited to, docetaxel, vinblastine, vincristine, vindesine and epothilone D. After waiting for a period of time sufficient to allow development of a substantially efficacious response of the antimitotic, a formulation comprising a synergistic dose of a benzoquinone ansamycin together with a second sub-toxic dose of the antimitotic is administered. In general, the appropriate period of time sufficient to allow development of a substantially efficacious response to the antimitotic will depend upon the pharmacokinetics of the antimitotic, and will have been determined during clinical trials of therapy using the antimitotic alone. In one embodiment of the invention, the period of time sufficient to allow development of a substantially efficacious response to the antimitotic is between about 1 hour and 96 hours. In another aspect of the invention, the period of time sufficient to allow development of a substantially efficacious response to the antimitotic is between about 2 hours and 48 hours. In another embodiment of the invention, the period of time sufficient to allow development of a substantially efficacious response to the antimitotic is between about 4 hours and 24 hours.

As noted above, the combination of an HSP90 inhibitor and an antimitotic allows for the use of a lower therapeutic dose of the antimitotic for the treatment of cancer. That a lower dose of antimitotic is used oftentimes lessens the side effects observed in a subject. The lessened side effects can be measured both in terms of incidence and severity. Severity measures are provided through a grading process delineated by the National Cancer Institute (common toxicity criteria NCI CTC, Version 2). For instance, the incidence of side effects are typically reduced 10%. Oftentimes, the incidence is reduced 20%, 30%, 40% or 50%. Furthermore, the incidence of grade 3 or 4 toxicities for more common side effects associated with antimitotic administration (e.g., anemia, anorexia, diarrhea, fatigue, nausea and vomiting) is oftentimes reduced 10%, 20%, 30%, 40% or 50%.

Formulations used in the present invention may be in any suitable form, such as a solid, semisolid, or liquid form. See *Pharmaceutical Dosage Forms and Drug Delivery Systems*, 5$^{th}$ edition, Lippicott Williams & Wilkins (1991), incorporated herein by reference. In general the pharmaceutical preparation will contain one or more of the compounds of the present invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations in solid, semi-solid, or liquefied form. In addition, auxiliary stabilizing, thickening, and coloring agents and perfumes may be used. Where applicable, the compounds useful in the methods of the invention may be formulated as microcapsules and nanoparticles. General protocols are described, for example, by Microcapsules and Nanoparticles in Medicine and Pharmacy by Max Donbrow, ed., CRC Press (1992) and by U.S. Pat. Nos. 5,510,118, 5,534,270 and 5,662,883 which are all incorporated herein by reference. By increasing the ratio of surface area to volume, these formulations allow for the oral delivery of compounds that would not otherwise be amenable to oral delivery. The compounds useful in the methods of the invention may also be formulated using other methods that have been previously used for low solubility drugs. For example, the compounds may form emulsions with vitamin E, or a PEGylated derivative thereof as described by PCT publications WO 98/30205 and WO 00/71163, each of which is incorporated herein by reference. Typically, the compound useful in the methods of the invention is dissolved in an aqueous solution containing ethanol (preferably less than 1% w/v). Vitamin E or a PEGylated-vitamin E is added. The ethanol is then removed to form a pre-emulsion that can be formulated for intravenous or oral routes of administration. Another method involves encapsulating the compounds useful in the methods of the invention in liposomes. Methods for forming liposomes as drug delivery vehicles are well known in the art. Suitable protocols include those described by U.S. Pat. Nos. 5,683,715, 5,415,869, and 5,424,073 which are incorporated herein by reference relating to another relatively low solubility cancer drug paclitaxel and by PCT Publication WO 01/10412 which is incorporated herein by reference relating to epothilone B. Of the various lipids that may be used, particularly preferred lipids for making encapsulated liposomes include phosphatidylcholine and polyethylenegly-col-derivatized distearyl phosphatidyl-ethanoloamine.

Yet another method involves formulating the compounds useful in the methods of the invention using polymers such as biopolymers or biocompatible (synthetic or naturally occurring) polymers. Biocompatible polymers can be categorized as biodegradable and non-biodegradable. Biodegradable polymers degrade in vivo as a function of chemical composition, method of manufacture, and implant structure. Illustrative examples of synthetic polymers include polyanhydrides, polyhydroxyacids such as polylactic acid, polyglycolic acids and copolymers thereof, polyesters, polyamides, polyorthoesters and some polyphosphazenes. Illustrative examples of naturally occurring polymers include proteins and polysaccharides such as collagen, hyaluronic acid, albumin, and gelatin.

Another method involves conjugating the compounds useful in the methods of the invention to a polymer that enhances aqueous solubility. Examples of suitable polymers include polyethylene glycol, poly-(d-glutamic acid), poly-(1-glutamic acid), poly-(1-glutamic acid), poly-(d-aspartic acid), poly-(1-aspartic acid) and copolymers thereof. Polyglutamic acids having molecular weights between about 5,000 to about 100,000 are preferred, with molecular weights between about 20,000 and 80,000 being more preferred wand with molecular weights between about 30,000 and 60,000 being most preferred. The polymer is conjugated via an ester linkage to one or more hydroxyls of an inventive geldanamycin using a protocol as essentially described by U.S. Pat. No. 5,977,163 which is incorporated herein by reference.

In another method, the compounds useful in the methods of the invention are conjugated to a monoclonal antibody. This method allows the targeting of the inventive compounds to specific targets. General protocols for the design and use of conjugated antibodies are described in *Monoclonal Antibody-Based Therapy of Cancer* by Michael L. Grossbard, ED. (1998), which is incorporated herein by reference.

The amount of active ingredient that may be combined with the carrier materials to produce a single dosage form will vary depending upon the subject treated and the particular mode of administration. For example, a formulation for intravenous use comprises an amount of the inventive compound ranging from about 1 mg/mL to about 25 mg/mL, preferably from about 5 mg/mL, and more preferably about 10 mg/mL. Intravenous formulations are typically diluted between about 2 fold and about 30 fold with normal saline or 5% dextrose solution prior to use.

Preferably, 17-AAG is formulated as a pharmaceutical solution formulation comprising 17-AAG in an concentration of up to 15 mg/mL dissolved in a vehicle comprising (i) a first component that is ethanol, in an amount of between about 40 and about 60 volume %; (ii) a second component that is a polyethoxylated castor oil, in an amount of between about 15 to about 50 volume %; and (iii) a third component that is selected from the group consisting of propylene glycol, PEG 300, PEG 400, glycerol, and combinations thereof, in an amount of between about 0 and about 35 volume %. The aforesaid percentages are volume/volume percentages based on the combined volumes of the first, second, and third components. The lower limit of about 0 volume % for the third component means that it is an optional component; that is, it may be absent. The pharmaceutical solution formulation is then diluted into water to prepare a diluted formulation containing up to 3 mg/mL 17-AAG, for intravenous formulation.

Preferably, the second component is Cremophor EL and the third component is propylene glycol. In an especially preferred formulation, the percentages of the first, second, and third components are 50%, 20-30%, and 20-30%, respectively.

Other formulations designed for 17-AAG are described in Tabibi et al., U.S. Pat. No. 6,682,758 B1 (2004) and Ulm et al., WO 03/086381 A1 (2003); the disclosures of which are incorporated herein by reference.

The method of the present invention is used for the treatment of cancer. In one embodiment, the methods of the present invention are used to treat cancers of the head and neck, which include, but are not limited to, tumors of the nasal cavity, paranasal sinuses, nasopharynx, oral cavity, oropharynx, larynx, hypopharynx, salivary glands, and paragangliomas. In another embodiment, the compounds of the present invention are used to treat cancers of the liver and biliary tree, particularly hepatocellular carcinoma. In another embodiment, the compounds of the present invention are used to treat intestinal cancers, particularly colorectal cancer. In another embodiment, the compounds of the present invention are used to treat ovarian cancer. In another embodiment, the compounds of the present invention are used to treat small cell and non-small cell lung cancer. In another embodiment, the compounds of the present invention are used to treat breast cancer. In another embodiment, the compounds of the present invention are used to treat sarcomas, including fibrosarcoma, malignant fibrous histiocytoma, embryonal rhabdomyosarcoma, leiomyosarcoma, neuro-fibrosarcoma, osteosarcoma, synovial sarcoma, liposarcoma, and alveolar soft part sarcoma. In another embodiment, the compounds of the present invention are used to treat neoplasms of the central nervous systems, particularly brain cancer. In another embodiment, the compounds of the present invention are used to treat lymphomas which include Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma.

EXAMPLES

The following Examples are provided to illustrate certain aspects of the present invention and to aid those of skill in the art in practicing the invention.

Materials and Methods

Cell Line and Reagents

Human colon adenocarcinoma cell line, DLD-1, and human breast adenocarcinoma cell line, SKBr-3, were obtained from American Type Culture Collection (manassas, Va.). DLD-1 cells were maintained in RPMI 1640 medium supplemented with 10% fetal bovine serum, and SKBr-3 cells were cultured in McCoy's 5a medium supplemented with 10% fetal bovine serum. 17-DMAG and 17-AAG were obtained using published procedures. Other cytotoxic agents were purchased commercially from suppliers such as Sigma Chemical Co. (St. Louis, Mo.) and Sequoia Research Products (Oxford, UK).

Cell Viability Assay and Combination Effect Analysis

Cells were seeded in duplicate in 96-well microtiter plates at a density of 5,000 cells per well and allowed to attach overnight. Cells were treated with 17-AAG or 17-DMAG and the corresponding antimitotic at varying concentrations, ranging from 0.5 picomolar ("pM") to 50 micromolar ("μM"), for 3 days. Cell viability was determined using the MTS assay (Promega). For the drug combination assay, cells were seeded in duplicate in 96-well plates (5,000 cells/well). After an overnight incubation, cells were treated with drug alone or a combination and the $IC_{50}$ value (the concentration of drug required to inhibit cell growth by 50%) was determined. Based on the $IC_{50}$ values of each individual drug, combined drug treatment was designed at constant ratios of two drugs, i.e., equivalent to the ratio of their $IC_{50}$. Two treatment schedules were used: In one schedule, the cells were exposed to 24 hours of 17-AAG or 17-DMAG. The drug was then added to the cells and incubated for 48 hours. In another schedule, cells were exposed to the drug alone for 24 hours followed by addition of 17-AAG or 17-DMAG for 48 hours. Cell viability was determined by the MTS assay.

Synergism, additivity or antagonism was determined by median effect analysis using the combination index (CI) calculated using Calcusyn (Biosoft, Cambridge, UK). The combination index is defined as follows:

$$CI=[D]_1/[D_x]_1+[D]_2/[D_x]_2$$

The quantities $[D]_1$ and $[D]_2$ represent the concentrations of the first and second drug, respectively, that in combination provide a response of x % in the assay. The quantities $[D_x]_1$ and $[D_x]_2$ represent the concentrations of the first and second drug, respectively, that when used alone provide a response of x % in the assay. Values of CI<1, CI=1, and CI>1 indicated drug-drug synergism, additivity, and antagonism respectively (Chou and Talalay 1984). The "enhancing" effect of two drugs can also be determined.

Results

17-AAG Combination in DLD-1 Cells

The following table provides CI values for combinations of 17-AAG and the antimitotics docetaxel, vinblastine, vincristine, vindesine, and epothilone D in a DLD-1 cell assay. "Pre-administration" refers to the administration of 17-AAG to the cells before the administration of antimitotic; "post-administration" refers to the administration of 17-AAG to the cells after the administration of antimitotic.

TABLE 5

CI values for combinations in DLD-1 cells
(human colorectal cancer cells).

| Antimitotic | 17-AAG Pre-Administration | 17-AAG Post-Administration |
|---|---|---|
| Docetaxel | 0.79 ± 0.15 | 0.29 ± 0.12 |
| Vinblastine | 0.92 ± 0.3 | 0.38 ± 0.11 |
| Vincristine | 0.96 ± 0.3 | 0.42 ± 0.08 |
| Vindesine | 0.91 ± 0.41 | 0.68 ± 0.08 |
| Epothilone D | 0.84 ± 0.06 | 0.61 ± 0.12 |

17-AAG Combination in SKSBr-3 Cells

The following table provides CI values for combinations of 17-AAG and the antimitotics docetaxel, vinblastine, vincristine, and epothilone D in an SKBr-3 cell assay.

TABLE 6

CI values for combinations in SKBr cells
(human breast cancer cells).

| Antimitotic | 17-AAG Pre-Administration | 17-AAG Post-Administration |
|---|---|---|
| Docetaxel | 0.53 ± 0.11 | 0.59 ± 0.26 |
| Vinblastine | 0.39 ± 0.03 | 0.68 ± 0.41 |
| Vincristine | 0.67 ± 0.37 | 0.99 ± 0.73 |
| Epothilone D | 0.72 ± 0.07 | 0.58 ± 0.009 |

Additional Observations

Additional analysis indicated that both 17-AAG and 17-DMAG reduced the expression of ErbB2 protein in SKBr3 and glioma cells. This observation, taken in combination with the results reported above, indicates that combinations of 17-AAG or 17-DMAG with any of the antimitotics above that are known to be useful to treat diseases characterized by elevated ErbB2 protein expression (i.e., levels of expressions of ErbB2 protein greater than those found in healthy cells).

The invention claimed is:

1. A method for treating colorectal cancer in a patient suffering from colorectal cancer, wherein the method comprises administering 17-(allylamino)-17-desmethoxygeldanamycin (17-AAG) and an antimitotic selected from the group consisting of docetaxel, vinbiastine, vincristine, vindestine, and epothilone D to a patient suffering from colorectal cancer, wherein the patient is exposed first to 24 hours of 17-AAG followed by exposure to 48 hours of the antimitotic, and further wherein the 17-AAG and the antimitotic are administered to the patient at a concentration equivalent to a ratio of corresponding $IC_{50}$ values of said 17-AAG and antimitotic.

2. A method for treating colorectal cancer in a patient suffering from colorectal cancer, wherein the method comprises administering 17-(allylamino)-17-desmethoxygeldanamycin (17-AAG) and an antimitotic selected from the group consisting of docetaxel, vinblastine, vincristine, vindestine, and epothilone D to a patient suffering from colorectal cancer, wherein the patient is exposed first to 24 hours of antimitotic followed by exposure to 48 hours of 17-AAG, and further wherein the 17-AAG and the antimitotic are administered to the patient at a concentration equivalent to a ratio of corresponding $IC_{50}$ values of said 17-AAG and antimitotic.

* * * * *